United States Patent
Rohl et al.

(10) Patent No.: US 10,716,621 B2
(45) Date of Patent: Jul. 21, 2020

(54) STENOSIS PREVENTION AND ABLATION DELIVERY SYSTEM

(71) Applicants: Boston Scientific Scimed Inc., Maple Grove, MN (US); Mayo Foundation for Medical Education and Research, Rochester, MN (US)

(72) Inventors: James P. Rohl, Prescott, WI (US); Douglas Pennington, Stillwater, MN (US); David R. Wulfman, Minneapolis, MN (US); Joel T. Eggert, Plymouth, MN (US); Douglas D. Pagoria, Forest Lake, MN (US); Samuel J. Asirvatham, Rochester, MN (US); Adeniyi O. Aremu, Brooklyn Park, MN (US); James A. Klos, Bay City, WI (US); Todd College, Little Canada, MN (US); Suraj Kapa, Rochester, MN (US); Sarah M. Gruba, St. Joseph, MN (US); David R. Holmes, Rochester, MN (US)

(73) Assignees: Boston Scientific Scimed, Inc., Maple Grove, MN (US); Mayo Foundation for Medical Education and Research, Rochester, MN (US)

( * ) Notice: Subject to any disclaimer, the term of this patent is extended or adjusted under 35 U.S.C. 154(b) by 307 days.

(21) Appl. No.: 15/793,954

(22) Filed: Oct. 25, 2017

(65) Prior Publication Data
US 2018/0110563 A1   Apr. 26, 2018

Related U.S. Application Data

(60) Provisional application No. 62/413,249, filed on Oct. 26, 2016.

(51) Int. Cl.
*A61B 18/14* (2006.01)
*A61B 18/08* (2006.01)
(Continued)

(52) U.S. Cl.
CPC ........ *A61B 18/1492* (2013.01); *A61B 18/082* (2013.01); *A61B 18/1445* (2013.01);
(Continued)

(58) Field of Classification Search
CPC .. A61B 2018/0022; A61B 2018/00238; A61B 2018/00255; A61B 2018/00285;
(Continued)

(56) References Cited

U.S. PATENT DOCUMENTS

| 5,423,744 A | 6/1995 | Gencheff et al. |
| 5,961,513 A * | 10/1999 | Swanson ............ A61B 18/1492 606/34 |

(Continued)

FOREIGN PATENT DOCUMENTS

WO   2014189887 A2   11/2014

OTHER PUBLICATIONS

International Search Report and Written Opinion issued in PCT/US2017/058376, dated Feb. 1, 2018, 11 pages.
International Preliminary Report on Patentability issued in PCT/US2017/058376, dated May 9, 2019, 8 pages.

*Primary Examiner* — Michael F Peffley
(74) *Attorney, Agent, or Firm* — Faegre Drinker Biddle & Reath LLP

(57) ABSTRACT

Various aspects of the present disclosure are directed toward apparatuses, systems, and methods for applying ablation therapy to a tissue region. The apparatuses, systems, and methods may include a balloon structure and one or more electrodes arranged on or within the balloon structure and configured to deliver energy to the tissue region.

20 Claims, 12 Drawing Sheets

(51) Int. Cl.
*A61M 25/10* (2013.01)
*A61B 18/00* (2006.01)
*A61B 5/046* (2006.01)

(52) U.S. Cl.
CPC ............. *A61M 25/10* (2013.01); *A61B 5/046* (2013.01); *A61B 2018/0022* (2013.01); *A61B 2018/00029* (2013.01); *A61B 2018/00065* (2013.01); *A61B 2018/00125* (2013.01); *A61B 2018/00238* (2013.01); *A61B 2018/00255* (2013.01); *A61B 2018/00285* (2013.01); *A61B 2018/00351* (2013.01); *A61B 2018/00577* (2013.01); *A61B 2018/1472* (2013.01); *A61M 25/1011* (2013.01); *A61M 2025/105* (2013.01); *A61M 2025/1013* (2013.01); *A61M 2025/1072* (2013.01)

(58) Field of Classification Search
CPC ........... A61B 2018/00029; A61B 2018/00065; A61B 2018/00125; A61B 2018/00351; A61B 2018/00577; A61B 2018/1472; A61B 18/1445; A61B 18/1492; A61B 5/046; A61M 2025/1013; A61M 2025/105; A61M 2025/1072
See application file for complete search history.

(56) References Cited

U.S. PATENT DOCUMENTS

| | | | | |
|---|---|---|---|---|
| 6,500,174 | B1* | 12/2002 | Maguire | A61B 18/1492 606/41 |
| 6,529,756 | B1* | 3/2003 | Phan | A61B 18/1492 600/374 |
| 7,674,259 | B2* | 3/2010 | Shadduck | A61B 18/04 606/27 |
| 2002/0188289 | A1* | 12/2002 | Hegde | A61B 18/1492 606/41 |
| 2005/0010207 | A1* | 1/2005 | Swanson | A61B 18/1492 606/41 |
| 2005/0059965 | A1* | 3/2005 | Eberl | A61B 18/1492 606/41 |
| 2007/0032787 | A1* | 2/2007 | Hassett | A61B 18/1492 606/41 |
| 2009/0247933 | A1 | 10/2009 | Maor et al. | |
| 2010/0256629 | A1 | 10/2010 | Wylie et al. | |
| 2014/0357956 | A1* | 12/2014 | Salahieh | A61B 1/00181 600/160 |
| 2018/0110563 | A1 | 4/2018 | Rohl et al. | |

* cited by examiner

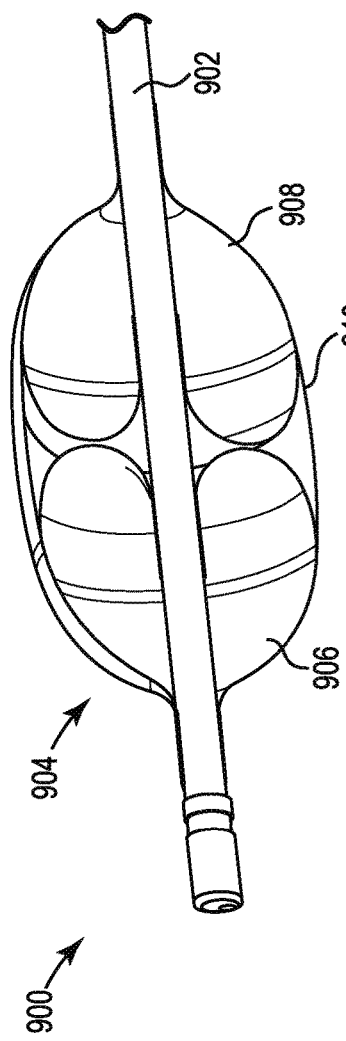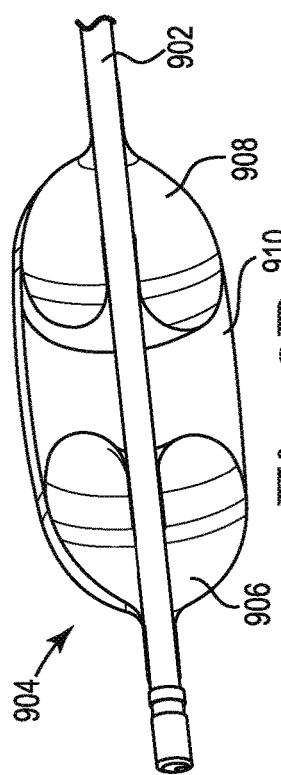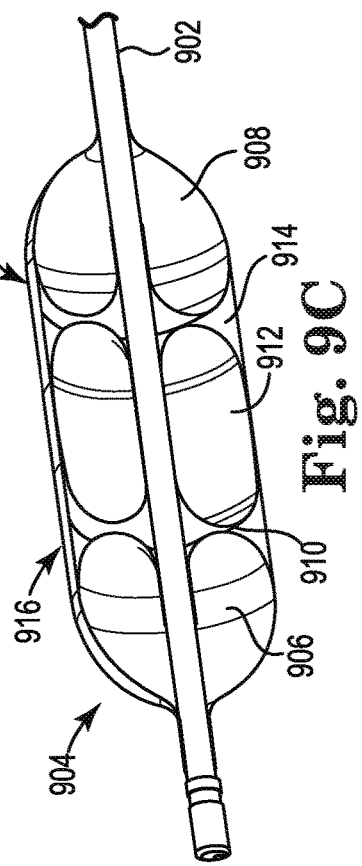

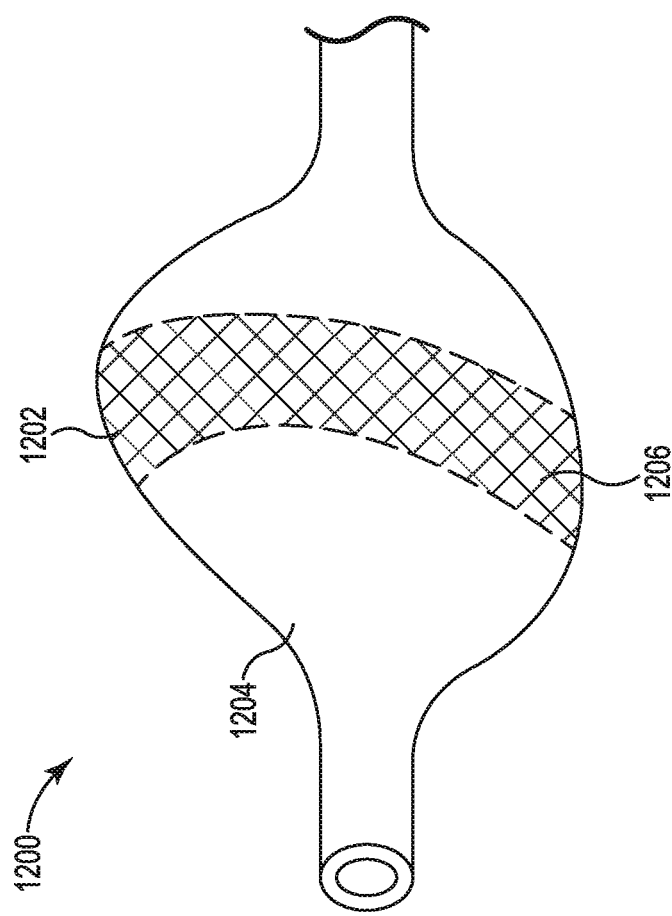

STENOSIS PREVENTION AND ABLATION DELIVERY SYSTEM

CROSS-REFERENCE TO RELATED APPLICATION

This application claims priority to Provisional Application No. 62/413,249, filed Oct. 26, 2016, which is herein incorporated by reference in its entirety.

TECHNICAL FIELD

The present disclosure generally relates to systems and methods for providing a therapy to a patient. More particularly, the present disclosure relates to apparatuses, systems, and methods for ablation delivery to tissue within the heart of the patient and stenosis reduction.

BACKGROUND

Atrial fibrillation is an irregular and often rapid heart rate that commonly causes poor blood flow to the body. Ablation procedures, including ablation of thoracic veins such as the pulmonary vein, may be a treatment for atrial fibrillation. During pulmonary vein ablation, for example, catheters are inserted into the atrium and energy is delivered to the tissue of the pulmonary vein and/or near the ostia of the pulmonary veins in the left atrium.

In certain instances, ablation may cause stenosis (e.g., narrowing of the vessels). Thus, it may be beneficial to include anti-stenotic elements in connection with or during the ablation procedure.

SUMMARY

In Example 1, an apparatus for applying ablation therapy to a tissue region, the apparatus comprising: a catheter sized and shaped for vascular access and including an elongate body extending between a proximal end and a distal end; a balloon structure arranged near the distal end of the elongate body and having a first portion with a first permeability and a second portion with a second permeability, the first permeability differing from the second permeability; and one or more electrodes arranged on or within the balloon structure and configured to deliver energy to the tissue region.

In Example 2, the apparatus of Example 1, wherein the first permeability is greater than the second permeability.

In Example 3, the apparatus of any of Examples 1-2, wherein the first portion of the balloon structure is configured to permeate a liquid therethrough and the second portion of the balloon structure is configured to anchor the elongate body at the tissue region.

In Example 4, the apparatus of Example 3, wherein the liquid comprises at least one of saline, a pharmacological agent, and an anti-stenotic agent.

In Example 5, the apparatus of any of Examples 1-4, wherein the balloon structure includes an external surface, and the first portion and the second portion are arranged along the external surface of the balloon.

In Example 6, the apparatus of Example 5, wherein the first portion of the balloon structure is configured to elute a liquid in response to inflation of the balloon structure.

In Example 7, the apparatus of any of Examples 5-6, wherein the first portion of the balloon structure comprises a plurality of nanostructures configured to contain the liquid.

In Example 8, the apparatus of any of Examples 1-4, wherein the second portion of the balloon structure is arranged within the first portion of the balloon structure.

In Example 9, the apparatus of Example 8, wherein the first portion forms a first chamber of the balloon structure, and the second portion forms a second chamber of the balloon structure.

In Example 10, the apparatus of Example 9, wherein the elongate body includes a first opening arranged within the first chamber and the elongate body includes a second opening arranged within the second chamber.

In Example 11, the apparatus of Example 10, wherein the first portion is configured to elute a liquid therethrough in response to influx of the liquid into the first chamber through the first opening.

In Example 12, the apparatus of Example 11, wherein the second portion is configured to expand and anchor the elongate body at the tissue region in response to influx of a liquid into the second chamber through the second opening.

In Example 13, the apparatus of any of Examples 1-11, wherein the first portion and the second portion form an external surface of the balloon structure.

In Example 14, the apparatus of any of Examples 1-13, wherein the one or more electrodes is arranged within the first portion of the balloon structure.

In Example 15, the apparatus of Example 14, wherein the elongate body includes a lumen, and the one or more electrodes is arranged within the lumen of the elongate body.

In Example 16, an apparatus for applying ablation therapy to a tissue region, the apparatus comprising: a catheter sized and shaped for vascular access and including an elongate body extending between a proximal end and a distal end; a balloon structure arranged near the distal end of the elongate body and having a first portion and a second portion, the first portion of the balloon structure being configured to permeate a liquid therethrough and the second portion of the balloon structure being configured to anchor the elongate body at the tissue region; and one or more electrodes arranged on or within the balloon structure and configured to deliver energy to the tissue region.

In Example 17, the apparatus of Example 16, wherein an external surface of the first portion of the balloon structure is configured to transfer the energy from the one or more electrodes to the tissue region.

In Example 18, the apparatus of Example 17, wherein the one or more electrodes comprises an electrode arranged within the first portion of the balloon structure.

In Example 19, the apparatus of Example 18, wherein the electrode is configured to deliver the energy via the first portion of the balloon structure in response to a direct current applied thereto.

In Example 20, the apparatus of Example 19, wherein the liquid comprises at least one of saline, a pharmacological agent, and an anti-stenotic agent, and the liquid is configured to mitigate against stenosis at the tissue region.

In Example 21, the apparatus of Example 16, wherein the second portion of the balloon structure is arranged within the first portion of the balloon structure.

In Example 22, the apparatus of Example 21, wherein the first portion forms a first chamber of the balloon structure, and the second portion forms a second chamber of the balloon structure.

In Example 23, the apparatus of Example 22, wherein the elongate body includes a first opening arranged within the first chamber and the elongate body includes a second opening arranged within the second chamber, the first portion is configured to elute a liquid therethrough in response to influx of the liquid into the first chamber through the first opening, and the second portion is configured to expand and anchor the elongate body at the tissue region in response to influx of a second liquid into the second chamber through the second opening.

In Example 24, the apparatus of Example 16, wherein the balloon structure is configured to telescope from the elongate body prior to inflation thereof.

In Example 25, the apparatus of Example 16, further comprising a steering mechanism configured to direct at least one of the balloon structure and the elongate body.

In Example 26, the apparatus of Example 25, wherein the steering mechanism comprises at least one wire coupled to a catheter handle.

In Example 27, an apparatus for applying ablation therapy to a tissue region, the apparatus comprising: a catheter sized and shaped for vascular access and including an elongate body extending between a proximal end and a distal end; a balloon structure arranged near the distal end of the elongate body and having a first portion with a first permeability and a second portion with a second permeability, the first permeability differing from the second permeability; and one or more electrodes arranged on or within the balloon structure configured to determine a target location for the ablation therapy and to deliver energy to the tissue region based on the determined location.

In Example 28, the apparatus of Example 27, wherein the first portion of the balloon structure is configured to elute a first liquid therethrough, and the first liquid is configured to mitigate against stenosis at the tissue region.

In Example 29, the apparatus of Example 28, wherein the second portion of the balloon structure is configured to anchor the elongate body at the tissue region in response to a second liquid expanding the second portion.

In Example 30, the apparatus of Example 29, further comprising a visualization element arranged with the elongate body, and the visualization element is configured to observe blood flow through the tissue area.

In Example 31, the apparatus of Example 30, wherein the tissue region is at least one of a pulmonary vein and a renal vein, and the first portion of the balloon structure and the one or more electrodes are configured to elute the first liquid and deliver the energy simultaneously.

In Example 32, a method for applying ablation therapy to a tissue region within a patient's heart, the method comprising: navigating a catheter within the patient's heart, the catheter including an elongate body extending between a proximal end and a distal end; positioning a balloon structure at the tissue region, the balloon structure being arranged near the distal end of the elongate body and having a first portion with a first permeability and a second portion with a second permeability, the first permeability differing from the second permeability; determining a pacing of the tissue region via one or more mapping electrodes arranged on or within the balloon structure to determine a target location for the ablation therapy; delivering energy to the tissue region based on the determined location via one or more electrodes arranged on or within the balloon structure; and eluting a liquid through the first portion of balloon structure during delivery of the energy to the tissue region.

In Example 33, the method of Example 32, further comprising anchoring the elongate body within the tissue region by inflating the second portion of the balloon structure.

In Example 34, the method of Example 33, further comprising visualizing flow within the tissue region subsequent to anchoring the elongate body within the tissue region In Example 35, the method of Example 32, wherein the liquid comprises at least one of saline, a pharmacological agent, and an anti-stenotic agent, and the liquid is configured to mitigate against stenosis at the tissue region. While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 9A shows a partial cross-sectional illustration of another exemplary apparatus for applying stenosis prevention to a tissue region having a first multiple chamber configuration in accordance with embodiments of the disclosure.

FIG. 9B shows the apparatus for applying stenosis prevention, as shown in FIG. 9A, having a second multiple chamber configuration in accordance with embodiments of the disclosure.

FIG. 9C shows the apparatus for applying stenosis prevention, as shown in FIGS. 9A-B, having a third multiple chamber configuration in accordance with embodiments of the disclosure.

FIG. 12 shows an exemplary balloon structure for applying stenosis prevention to a tissue region having a plurality of nanostructures in accordance with embodiments of the disclosure.

Figure 1:
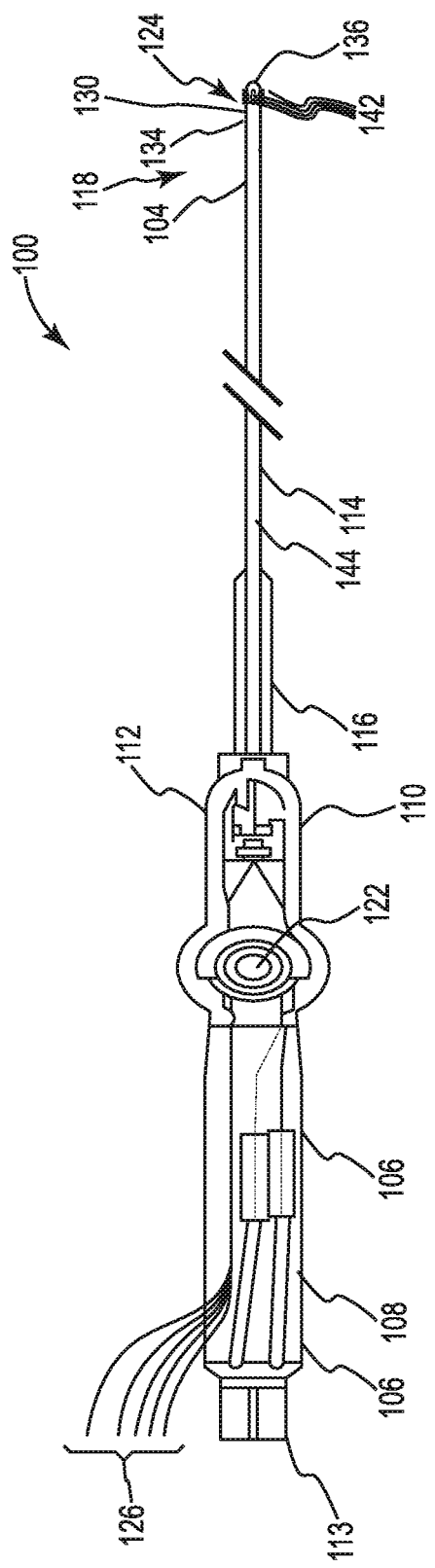
FIG. 1 shows an exemplary ablation system in accordance with embodiments of the disclosure.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 shows an exemplary ablation system 100 in accordance with embodiments of the disclosure. As shown, the system 100 includes a catheter 102 sized and shaped for vascular access. The catheter 102 has a distal end 104 and a proximal end 106. In one aspect, the proximal end 106 of the catheter 102 includes a handle 108 having a proximal portion 110 and a distal portion 112. A physician may use the manipulate the ablation system 100 via the handle 108 during a treatment procedure involving ablation. The handle 108 may include a plurality of conduits, conductors, and wires to facilitate control of the catheter 102 and/or mating of the catheter 102 with a source of fluid, a source of ablative energy, a source of mapping, temperature display, sensors, and/or control software/hardware. The handle 108 further includes a connection port 113 through which ablative energy source and a mapping energy source may be operably coupled.

The catheter 102 can include an elongate body 114 having a proximal end 116 and a distal end 118. The elongate body 114 may house electrical conductors/cable assembly (e.g., wires) for transmitting sensed signals and/or ablation energy. In addition, the elongate body 114 may include a circular cross-sectional geometry. However, other cross-sectional shapes, such as elliptical, rectangular, triangular, and various other shapes, can be provided. In certain instances, the elongate body 114 may be preformed of an inert, resilient material that retains its shape and does not soften significantly at body temperature; for example, Pebax®, polyethylene, or Hytrel® (polyester). The elongate body 114 may be made of a variety of materials, including, but not limited to, metals and polymers. The elongate body 114 may be flexible and capable of winding through a tortuous path that leads to a target site, i.e., an area within the heart. The elongate body 114 may also be semi-rigid, i.e., by being made of a stiff material, or by being reinforced with a coating or coil, to limit the amount of flexing.

In certain instances, the movement of the distal end 118 of the elongate body 114 (such as to wind through the tortuous path that leads to a target site) can be controlled by a control mechanism 122 included within the handle 108. The system 100 can include an articulating section of the elongate body 114 (e.g., near the distal end 118) that is controlled via the control mechanism 122. The distal end 118 of the elongate body 114 may be deflected or bent. The articulation section of the body may facilitate insertion of the catheter 102 through a body lumen (e.g., vasculature) and/or placement of electrodes at a target tissue location. The articulation may provide one or more degrees of freedom and permit up/down and/or left/right articulation.

The distal end 104 of the catheter 102 includes a tip section 124 positioned at the distal end 118 of the elongate body 114. The tip section 124 includes a proximal portion 134 and a distal portion 136. In certain instances, portions of the tip section 124 may be formed from a conductive material. More specifically, the system 100 includes one or more electrode structures 142, formed of the conductive material, on an exterior surface 130 of the tip section 124. The electrode structures 142 may be arranged around a circumference of exterior surface 130 of the tip section 124. In addition, the electrode structures 142 may be configured as mapping electrodes and ablation electrodes.

The electrode structures 142 may be configured to conduct radio frequency (RF) energy or direct current to form lesions during the ablation procedure. The electrode structures 142 may deliver ablation energy to the myocardial tissues that are the source of arrhythmia, thereby destroying them or a portion thereof through heat. Each of the electrode structures 142 may be coupled to wires 126 using suitable means, such as soldering or welding. The number of wires 126 may be equal to the number of electrode structures 142. The wires 126 can pass through a lumen 144 extending through the elongate body 114 of the catheter 102 and are electrically coupled to the RF generator exteriorly coupled to the ablation system 100.

The electrode structures 142 may also be configured to measure the localized intracardial electrical activity (map) in real time at the point of RF energy delivery. The electrode structures 142 allow the physician to ascertain lesion formation by measuring the electrical activity of the tissue having been in contact with an ablation electrode (e.g., the lack of electrical activity indicates ablated tissue, whereas the presence of electrical activity indicates live or non-ablated tissue). In certain instances, the wires 126, coupled to the electrode structures 142, may also be electrically coupled to a mapping signal processor such that electrical events in myocardial tissue can be sensed for the generation of electrograms, monophasic action potentials (MAPs), isochronal electrical activity maps, and the like.

Figure 2:
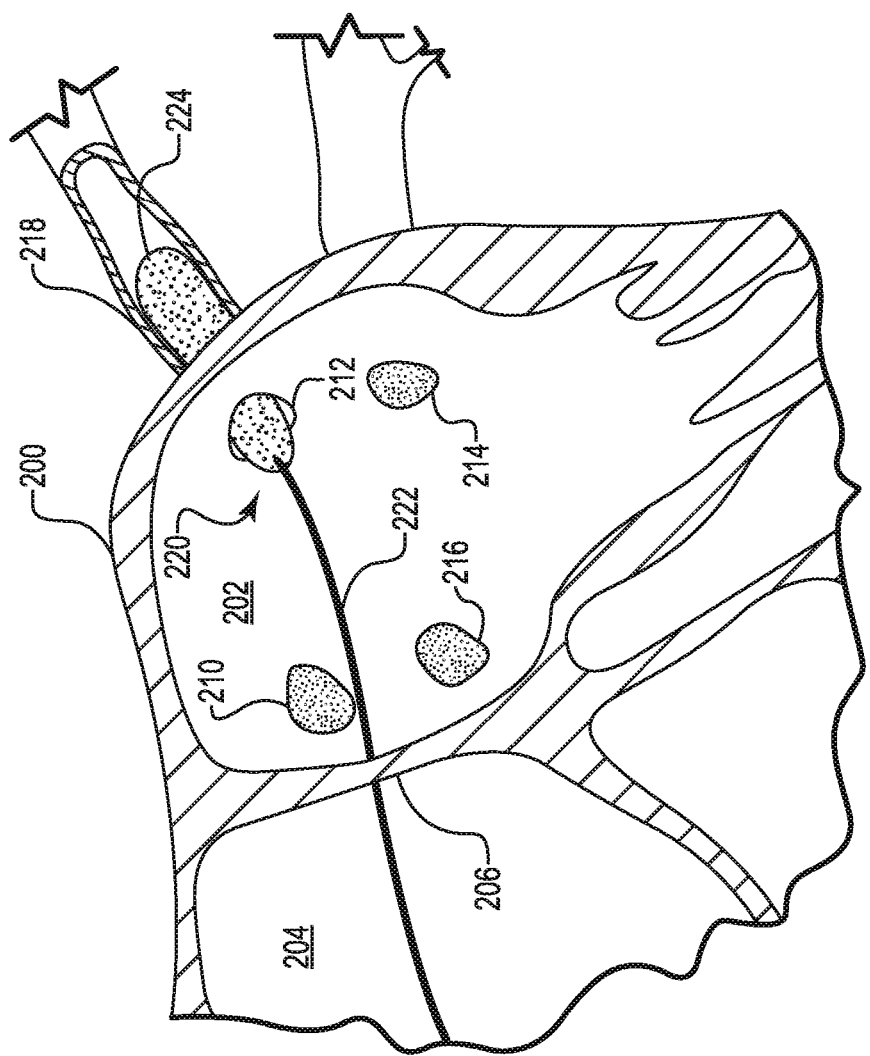
FIG. 2 shows an exemplary ablation system at a target tissue region within patient's heart in accordance with embodiments of the disclosure.

FIG. 2 shows an exemplary ablation system at a target tissue region within patient's heart 200 in accordance with embodiments of the disclosure. More specifically, the heart 200 shown in FIG. 2 may be undergoing a pulmonary vein ablation procedure using a device 220 in accordance with various aspects discussed herein. The device 220 may include a catheter having an elongate body 222 that is connected to a balloon structure 224. The device 220 may be connected to an ablation energy source and controller (e.g., radiofrequency (RF) or direct current (DC) system not shown) and one or more liquid sources (not shown), both of which are located external to the patient. The balloon structure 224 may be located near the distal end of elongate body 222. One or more interior chambers of the balloon structure 224 may be in fluid communication with a liquid delivery lumen arranged within the elongate body 222. The liquid delivery lumen is used to convey the one or more liquids from the source external to the patient into the balloon structure 224. The elongate body 222 and the balloon structure 224 may be delivered to a tissue region to which ablation energy may be applied.

As shown in FIG. 2, the elongate body 222 may be positioned in the left atrium 202 of the patient's heart 200. More specifically and in certain instances, the device 220 may enter the right atrium 204 of heart 200 through a femoral vein and the inferior vena cava (not shown). The device 220 may be passed through a puncture in an atrial septum 206 to access left atrium 202. From the left atrium 202, the balloon catheter device 220 may be positioned through any of the pulmonary vein ostia 210, 212, 214, or 216 to enter a pulmonary vein such as pulmonary vein 218. In certain instances the device 220 may be an over-the-wire device that is delivered over or on a pre-placed guidewire or a delivery catheter/sheath or rapid exchange catheter may be used to assist in the insertion and placement of the device 220.

After positioning of the device 220 at the tissue region (within the pulmonary vein 218 as shown in FIG. 2), the balloon structure 224 may be expanded. The balloon structure 224 may be inflated using a liquid (e.g., saline, a pharmacological agent, or a combination thereof) as the inflation medium. In instances where the balloon structure 224 is positioned within a vessel such as the pulmonary vein 218, the inflation of balloon structure 224 may cause the outer surface of balloon structure 224 to contact an inner wall of vessel such as the pulmonary vein 218. In certain instances, ablation energy may be applied through one or more electrodes (not shown) arranged within the balloon structure 224 to initiate the modulation of target neural fibers. In addition, one or more portions of the balloon structure 224 may have a permeability such that a liquid may exude, elute, weep, or otherwise be transmitted from therethrough. In certain instances, the liquid may be an anti-stenotic pharmaceutical agent that may contact the inner wall of pulmonary vein 218.

The ablation energy may be applied through one or more portions of the balloon structure 224 by an electric field generated by the external source/controller and transferred through wires within one or more lumens of the elongate body 222 to electrodes (not shown) arranged with the balloon structure 224. The electric energy can be transmitted to the inner wall of pulmonary vein 218 directly from the electrodes on the surface of balloon structure 224 or from the electrodes within the balloon structure 224 via the liquid (pharmacological agent) that exudes from the exterior surface of balloon structure 224. The electric field may modulate the activity along neural fibers within the wall of the pulmonary vein 218 by at least partially causing apoptotic cell death to the tissue receiving the ablation energy. In certain instances while the electric field for ablation is being applied, transmission of the liquid (pharmacological agent) from the balloon structure 224 to the tissue can be continued. The ablation process may be performed simultaneously and concurrently with the delivery of an antimitotic pharmacological agent to the tissue receiving the ablation energy or the ablation process can be performed sequentially with the delivery of the liquid.

Delivering the pharmacological agent prior to the ablative energy may provide iontophoresis-like action to drive the agent into the tissue. Delivering the ablative energy prior to the pharmacological agent can provide some electroporative disruption of the endothelial cell-to-cell junction, and thereby promote delivery of the agent. In certain instances, a repetitious cyclic delivery of ablative energy and the pharmacological agent may enhance uptake of the agent. In certain instances, the pharmacological agent can have an ionic base so as to optimize the ablative energy's ability to get the agent beyond the endothelium of the tissue. Paclitaxel is an example of one type of antimitotic pharmacological agent that may be used with the apparatuses, systems, and methods discussed herein. This technique of coordinating the delivery of paclitaxel with the ablation process may prevent or reduce the occurrence of fibrosis, stenosis, and neointimal hyperplasia of the tissue undergoing ablation.

In certain instances, the electric field may be generated by applying direct current to the one or more electrodes arranged within the balloon structure 224. Application of direct current, which is athermal, may be less likely to cause stenosis as compared to RF ablation. In certain instances, the amount of anti-stenotic pharmaceutical agent released from the balloon structure 224 may be tailored based on the type of energy used for ablation (e.g., a greater amount of anti-stenotic for RF ablation as compared to the amount of anti-stenotic for direct current). In addition, the use of direct current may cause apoptotic cell death to the tissue receiving the ablation energy. The direct current may form pores in the cells of the wall of the pulmonary vein 218 that are irreversible (e.g., the pores do not close). The balloon structure 224 being in contact with the wall of the pulmonary vein 218 may provide controlled and direct ablation of a target area while mitigating against down-stream proliferation of the ablation energy.

Figure 3:
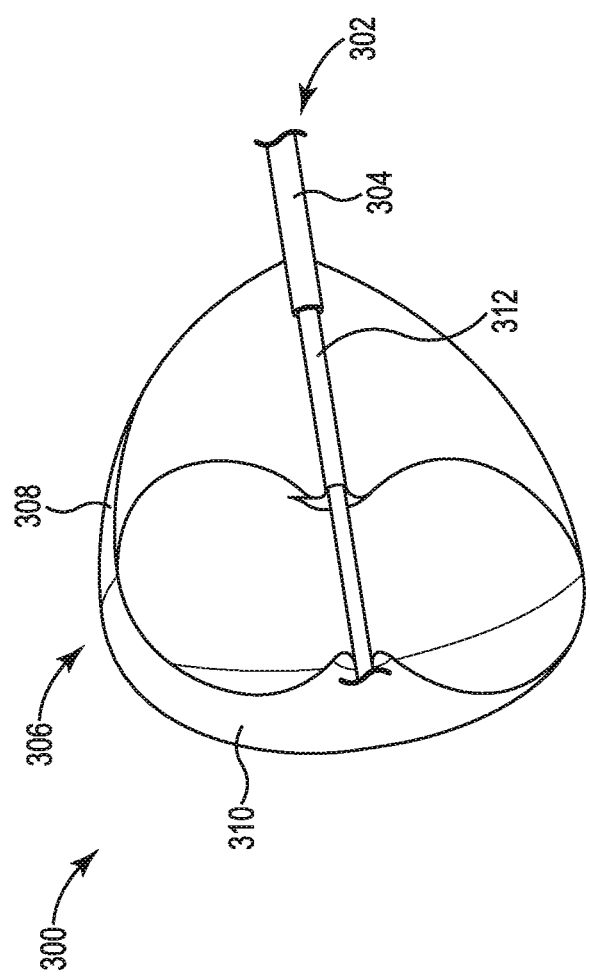
FIG. 3 shows a partial cross-sectional illustration of an exemplary apparatus for applying ablation therapy to a tissue region in accordance with embodiments of the disclosure.

FIG. 3 shows a partial cross-sectional illustration of an exemplary apparatus 300 for applying ablation therapy to a tissue region in accordance with embodiments of the disclosure. The apparatus 300 may include a catheter 302 sized and shaped for vascular access that has an elongate body 304 extending between a proximal end and a distal end of the catheter 302. A distal portion of the catheter 302 and the elongate body 304 is shown in FIG. 3. The apparatus 300 may also include a balloon structure 306 arranged near the distal end of the elongate body 304. The balloon structure 306 may include a first portion 308 and a second portion 310. The balloon structure 306 may be configured to inflate in response to a liquid or inflation medium being provided thereto. In certain instances, the first portion 308 and the second portion 310 may be separately inflated using two inflation mediums or the first portion 308 and the second portion 310 may be inflated using a single inflation medium.

In certain instances, the first portion 308 of the balloon structure 306 may include a first permeability and the second portion 310 of the balloon structure 306 may include a second permeability. The first permeability may differ from the second permeability. More specifically, the first permeability may be greater than the second permeability. As a result and in certain instances, the first portion 308 of the balloon structure 306 may be configured to permeate a liquid therethrough. As the first portion 308 of the balloon structure 306 is inflated, the liquid may permeate therethrough. The liquid may be saline, a pharmacological agent, an anti-stenotic agent, or a combination thereof.

In certain instances, the first portion 308 of the balloon structure 306 may form a first chamber, and the second portion 310 of the balloon structure 306 may form a second chamber. As a result, the first portion 308 and the second portion 310 may be separate and distinct structures. More specifically, the second portion 310 may be a balloon or other similar structure that is arranged within the first portion 308. The first portion 308 may be deposited or attached onto the second portion 310.

The apparatus 300 may also include one or more electrodes arranged on or within the balloon structure 306. As shown in FIG. 3, the apparatus includes an electrode 312 arranged within the balloon structure 306. The electrode 312 may be configured to deliver energy to a tissue region. In certain instances, the electrode 312 may be configured to delivery energy in response to a direct current applied thereto.

Figure 4:
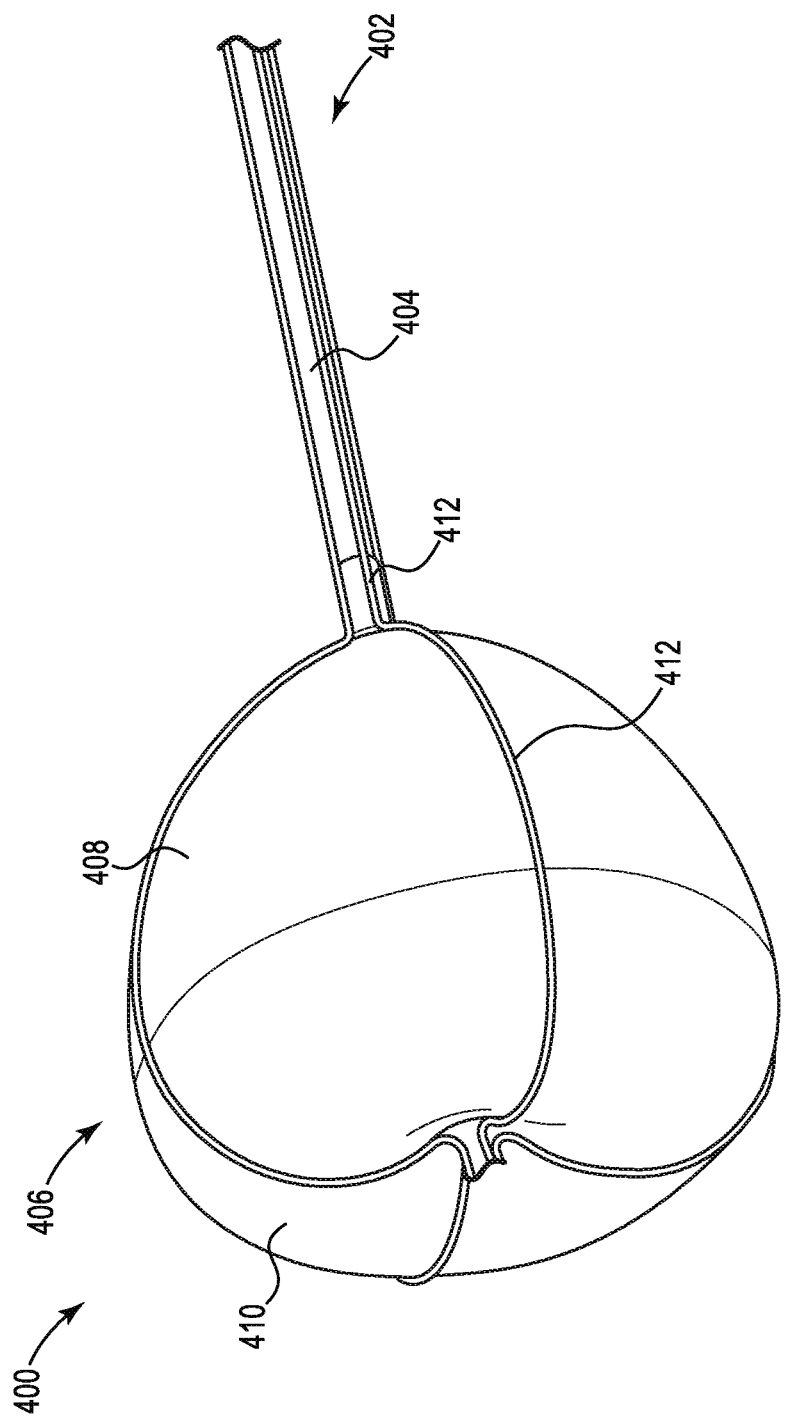
FIG. 4 shows an exemplary apparatus for applying ablation therapy to a tissue region in accordance with embodiments of the disclosure.

FIG. 4 shows an exemplary apparatus 400 for applying ablation therapy to a tissue region in accordance with embodiments of the disclosure. The apparatus 400 may include a catheter 402 having an elongate body 404. A distal portion of the catheter 402 and the elongate body 404 is shown in FIG. 4. The apparatus 400 may also include a balloon structure 406 arranged near the distal end of the elongate body 404. The balloon structure 406 may include a first portion 408 having a first permeability and a second portion 410 having a second permeability. The balloon structure 406 may be configured to inflate in response to a liquid or inflation medium being provided thereto. The first permeability may differ from the second permeability such that the first permeability may be greater than the second permeability. As a result and in certain instances, the first portion 408 of the balloon structure 406 may be configured to permeate a liquid therethrough, and the second portion 410 may mitigate against liquid permeation or eluting. Thus, as the balloon structure 406 is inflated, the liquid may permeate through the first portion 408. The liquid may be saline, a pharmacological agent, an anti-stenotic agent, or a combination thereof.

The apparatus 400 also includes electrodes 412 arranged on an exterior surface of the balloon structure 406. The electrodes 412 may be arranged along the elongate body 404 and configured to deliver energy to a tissue region. The electrodes 404 may also be arranged uniformly or non-uniformly about the circumference of the balloon structure 406. In certain instances, the electrodes 412 may be configured to delivery energy in response to a direct current applied thereto. Energy may be delivered simultaneously/concurrently on the electrodes 412 or sequentially across the electrodes 412 via radiofrequency energy, electroporation, vibration, ultrasound or laser energy.

Figure 5:
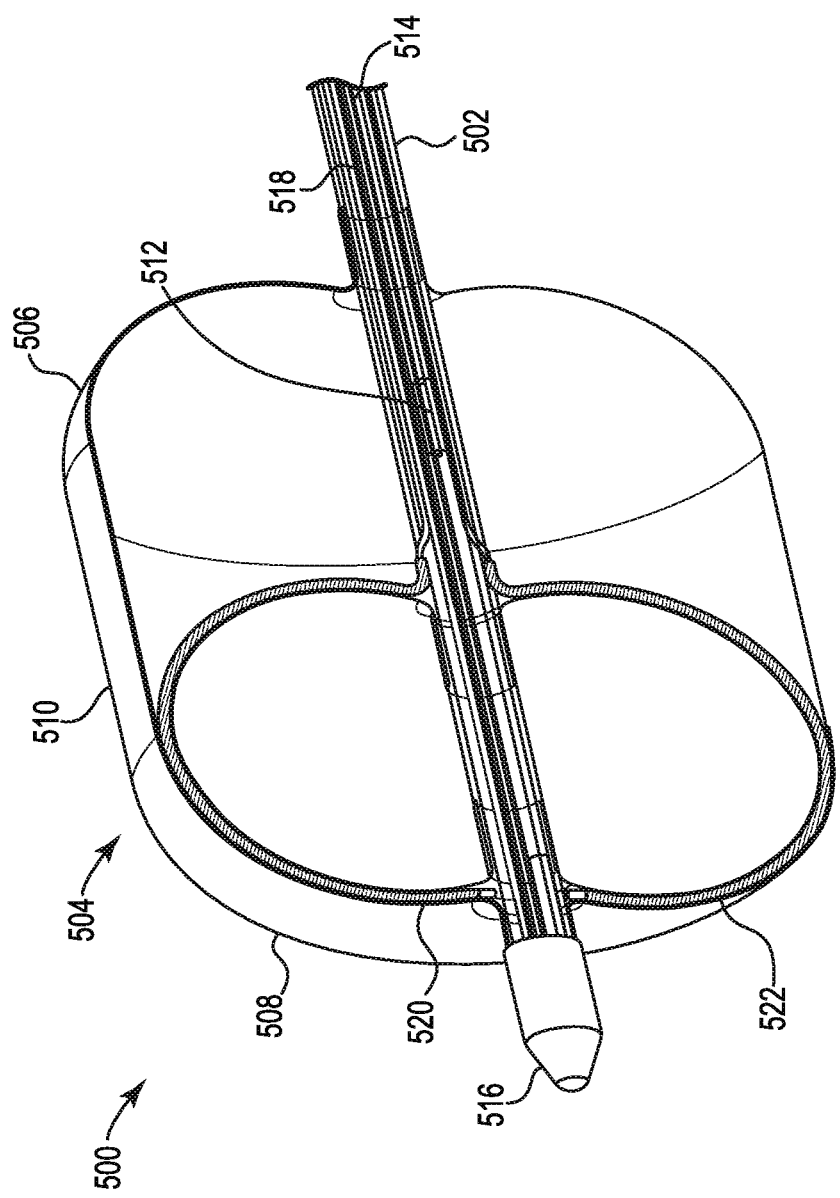
FIG. 5 shows a partial cross-sectional illustration of another exemplary apparatus for applying ablation therapy to a tissue region in accordance with embodiments of the disclosure.

FIG. 5 shows a partial cross-sectional illustration of another exemplary apparatus 500 for applying ablation therapy to a tissue region in accordance with embodiments of the disclosure. The apparatus 500 includes a catheter having an elongate body 502. At or near a distal portion of the elongate body 502 is a balloon structure 504. The balloon structure 504 may be attached to or formed on the elongate body 502.

The balloon structure 504 may include a first portion 506, at least a section of which includes a first permeability, and a second portion 508 having a second permeability. The balloon structure 504 may be configured to inflate in response to a liquid or inflation medium being provided thereto. As a result, the first permeability may be greater than the second permeability. Thus, in certain instances, the first portion 506 of the balloon structure 504 may be configured to permeate a liquid therethrough (in response to inflation of the balloon structure 504) and the second portion 508 of the balloon structure 504 may be to anchor the elongate body 502 at a tissue region. The first portion 506 and the second portion 508 are arranged along an external surface of the balloon structure 504.

In addition, the first portion 506 of the balloon structure 504 may form a first chamber, and the second portion 508 of the balloon structure 504 may form a second chamber. The second portion 508 may be a balloon or other similar structure that is arranged within the first portion 506. The first portion 506 may be deposited or attached onto the second portion 508. As noted above, at least a section of the first portion 506 has a greater permeability than the second portion 508. In certain instances, the permeability of the second portion 508 may be zero such that liquid does not permeate or elute therethrough. Although the entirety of the balloon structure 504 is configured to inflate, the balloon structure 504 includes a section, the second portion 508, that may be impermeable to liquid. Thus, at least a section 510 of the balloon structure 504 that does not include the second portion 508 may be permeable. The first portion 506 may be formed of the same permeability such that the entirety of the first portion 506 may permeate liquid therethrough, or the section 510 of the first portion 506 may permeate liquid therethrough.

The balloon structure 504 may be positioned at a target tissue region for ablation. In certain instances, the tissue region may be a vessel such as a pulmonary vein or a renal vein or other appendage. The balloon structure 504 may be configured to deploy within the vessel such that the section 510 contacts the vessel wall. The first portion 506 may permeate the liquid to the tissue region (e.g., the vessel wall). The liquid may include an anti-stenotic agent that mitigates against stenosis at the tissue region. In addition, the second portion 508 may be configured to anchor the elongate body 502 at the tissue region. The second portion 508 may be impermeable to the liquid.

The apparatus 500 may also include an electrode 512 arranged within the balloon structure 504. The electrode 512 may be configured to deliver energy to a tissue region. In certain instances, the electrode 512 may be arranged within the first portion 506 and configured to delivery energy in response to a direct current applied thereto. The ablation energy from the electrode 512 may be applied through an external surface of the first portion 506 of the balloon structure 504 by an electric field generated by the external source/controller and transferred through a wire 514 within the elongate body 502. The electric energy can be transmitted to the tissue region (e.g., the vessel wall) via the liquid, which may include an anti-stenotic agent, that exudes from the first portion 506 of the balloon structure 504. The electric field may modulate the activity along neural fibers within the wall of the tissue by at least partially causing apoptotic cell death to the tissue receiving the ablation energy. In certain instances while the electric field for ablation is being applied, transmission of the liquid, including the anti-stenotic agent, from the first portion 506 of the balloon structure 504 to the tissue can be continued. The ablation process applied via the electrode 512 may be performed simultaneously and concurrently with the delivery of an antimitotic pharmacological agent to the tissue receiving the ablation energy or the ablation process can be performed sequentially with the delivery of the liquid.

In certain instances and as noted above, the electric field may be generated by applying direct current to the electrode 512. The use of direct current may cause apoptotic cell death to the tissue receiving the ablation energy. The direct current may form pores in the cells of the tissue region such that are irreversible (e.g., the pores do not close). The balloon structure 504 being in contact with the tissue may provide controlled and direct ablation of a target area while mitigating against down-stream proliferation of the ablation energy.

The apparatus 500 may also include a tip electrode 516 that is configured to form a ground or a closed-loop with the electrode 512. Similar to the electrode 512, the tip electrode 516 may be coupled to the external source/controller via a wire 518 within the elongate body 502. The external source/controller may apply RF ablation energy or DC current. Thus, the tip electrode 516 may function as a single point ablation electrode when the external source/controller is configured to apply RF ablation energy.

Figure 7:
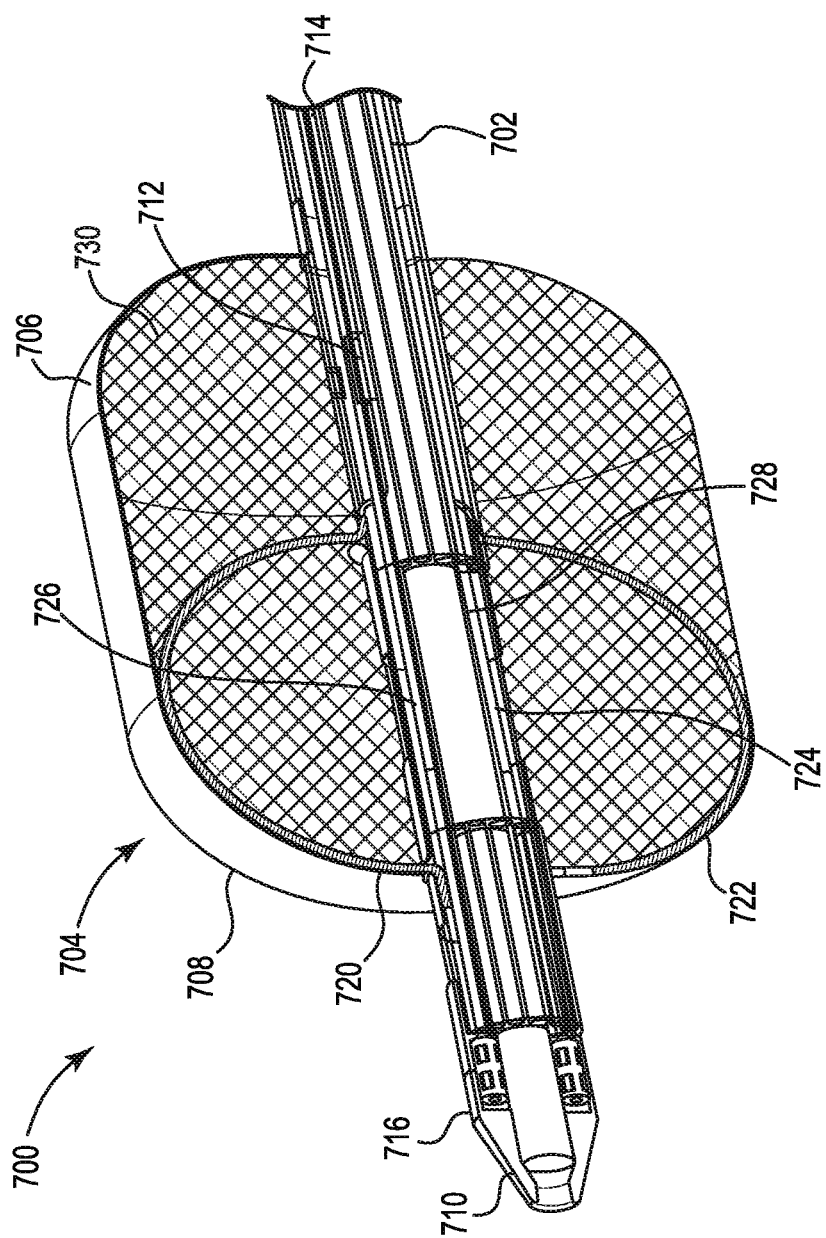
FIG. 7 shows a partial cross-sectional illustration of another exemplary apparatus for applying ablation therapy to a tissue region having a steering mechanism in accordance with embodiments of the disclosure.
Figure 8:
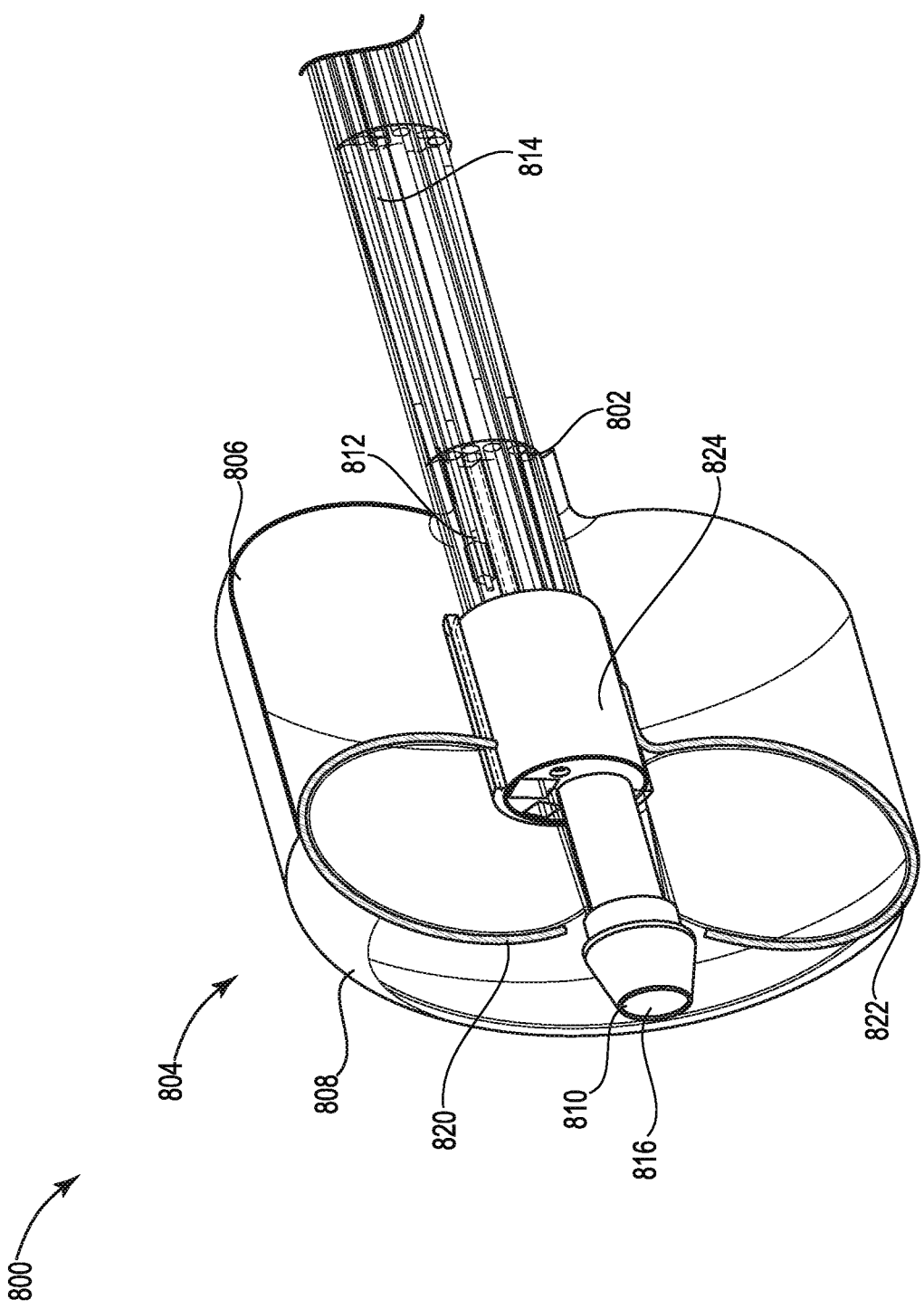
FIG. 8 shows a partial cross-sectional illustration of another exemplary apparatus for applying ablation therapy to a tissue region having a visualization element in accordance with embodiments of the disclosure.

In certain instances, the electrode 512 and/or the tip electrode 516 may also be configured to measure the localized intracardial electrical activity. The wire 514 and/or the wire 518 may also be electrically coupled to a mapping signal processor such that electrical events in myocardial tissue can be sensed for the generation of electrograms, monophasic action potentials (MAPs), isochronal electrical activity maps, and the like. The electrode 512 and/or the tip electrode 516 may allow the physician to measure the electrical activity of the tissue region (e.g., the lack of electrical activity indicates ablated tissue, whereas the presence of electrical activity indicates live tissue). In certain instances, the tip electrode 516 may include a hole (e.g., as shown in FIGS. 7-8) centrally a distal end thereof for interfacing with a guide wire or for contrast to be ejected therethrough. In addition, the tip electrode 516 may be collapsible (e.g., similar to an accordion) after entering into the tissue region. The tip electrode 516 may stabilize the apparatus 500 within the tissue region, and collapse if the balloon structure 504 is moved more distally within the tissue region. Collapsing the tip electrode 516 may facilitate positioning of the balloon structure 504 without increasing the pressure within the tissue region. In certain instances, the tip electrode 516 may be a mesh structure (e.g., formed from Nitinol) that may collapse and disperse the electrical energy over surface area of the mesh.

In other instances, the apparatus 500 may include pacing electrodes 520, 522. The pacing electrodes 520, 522 may be arranged within the balloon structure 504. In certain instances, the pacing electrodes 520, 522 are arranged within the second portion 508 of the balloon structure 504. The pacing electrodes 520, 522 may be electrically coupled to a mapping signal processor such that electrical events in myocardial tissue can be sensed for the generation of electrograms, monophasic action potentials (MAPs), isochronal electrical activity maps, and the like. The pacing electrodes 520, 522 may allow the physician to measure the electrical activity of the tissue region (e.g., the lack of electrical activity indicates ablated tissue, whereas the presence of electrical activity indicates live tissue). The ablation energy applied via the electrode 512 may be altered based on the electrical activity measured by the pacing electrodes 520, 522, used to determine a target location for the ablation therapy.

The illustrative components shown in FIG. 5 are not intended to suggest any limitation as to the scope of use or functionality of embodiments of the disclosed subject matter. Neither should the illustrative components be interpreted as having any dependency or requirement related to any single component or combination of components illustrated therein. Additionally, any one or more of the components depicted in any of the FIG. 5 may be, in embodiments, integrated with various other components depicted therein (and/or components not illustrated), all of which are considered to be within the ambit of the disclosed subject matter. For example, the pacing electrodes 520, 522 may be used in connection with apparatus 300 and apparatus 400.

Figure 6:
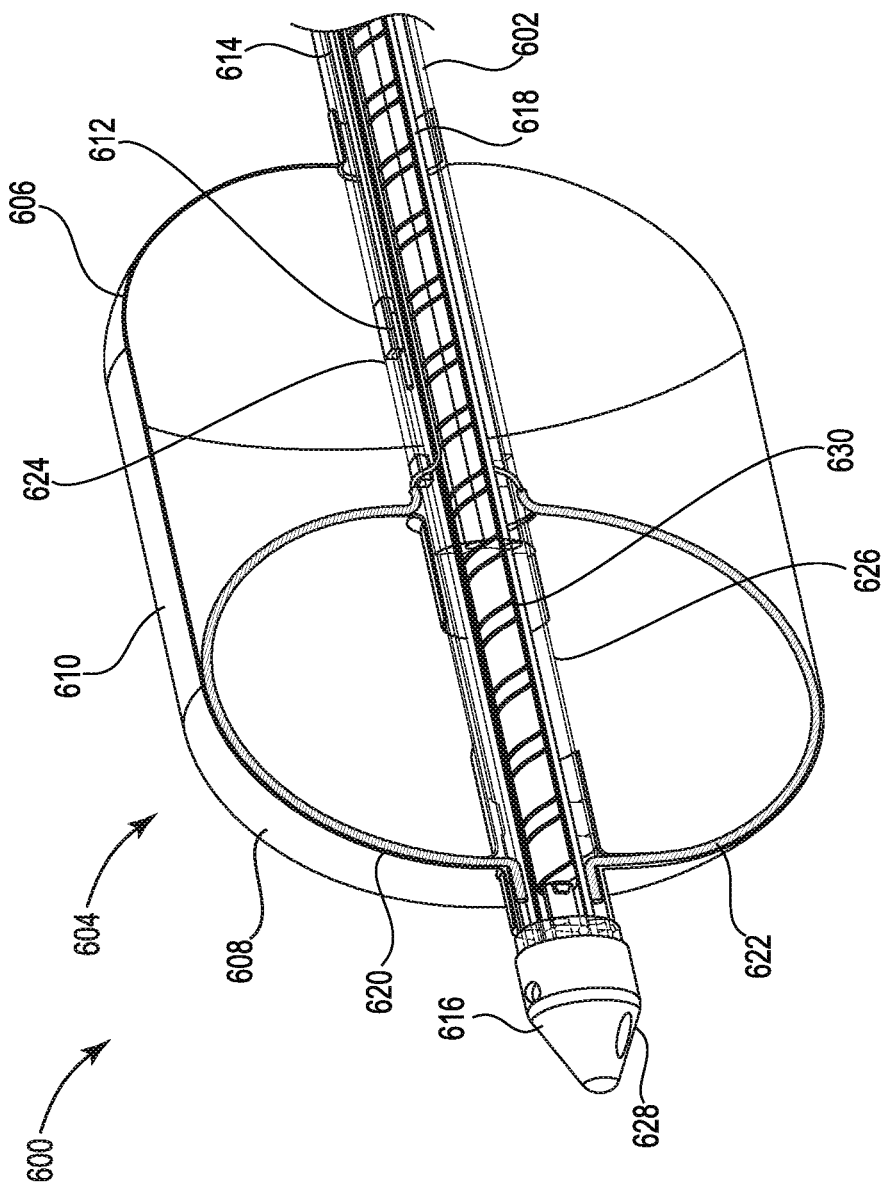
FIG. 6 shows a partial cross-sectional illustration of another exemplary apparatus for applying ablation therapy to a tissue region in accordance with embodiments of the disclosure.

FIG. 6 shows a partial cross-sectional illustration of another exemplary apparatus 600 for applying ablation therapy to a tissue region in accordance with embodiments of the disclosure. The apparatus 600 includes a catheter having an elongate body 602. The apparatus 600 also may include a balloon structure 604 arranged at or near a distal portion of the elongate body 602. The balloon structure 604 may be configured to inflate in response to a liquid or inflation medium being provided thereto. In addition, the balloon structure 604 may include a first portion 606 and a second portion 608. In certain instances, the first portion 606 of the balloon structure 604 may be configured to permeate a liquid therethrough (in response to inflation of the balloon structure 604) and the second portion 608 of the balloon structure 604 may be to anchor the elongate body 602 at the tissue region.

The balloon structure 604 may be positioned at or within the tissue region for ablation. In certain instances, the tissue region may be a vessel such as a pulmonary vein or a renal vein. The balloon structure 604 may be configured to deploy within the vessel such that section 610 contacts the vessel wall. The first portion 606 may permeate the liquid to the tissue region (e.g., the vessel wall). The liquid may include an anti-stenotic agent that mitigates against stenosis within the vessel. In addition, the second portion 608 may anchor the elongate body 602 within the vessel.

In certain instances, the elongate body 602 includes a first opening 624 arranged within the first portion 606 (or chamber) and the elongate body 602 includes a second opening 626 arranged within the second portion 608 (or chamber). The first portion 606 (or chamber) is configured to elute a liquid therethrough in response to influx of the liquid into the first portion 606 (or chamber) through the first opening 624. In addition, the second portion 608 may be configured to expand and anchor the elongate body 602 at the tissue region in response to influx of a liquid into the second portion 608 (or chamber) through the second opening 626. The liquid eluted through the first portion 606 may be configured to mitigate against stenosis at the tissue region.

In certain instances, the apparatus 600 may also include an electrode 612, arranged within a lumen of the elongate body 602, that is configured to deliver energy to a tissue region. In certain instances, the electrode 612 may be arranged within the first portion 606 and configured to delivery energy in response to a direct current applied thereto. The ablation energy from the electrode 612 may be applied through an external surface of the first portion 606 of the balloon structure 604 by an electric field generated by an external source/controller and transferred through a wire 614 within the elongate body 602. The apparatus 600 may also include a tip electrode 616 that is configured to form a ground or a closed-loop with the electrode 612. The tip electrode 616 may be coupled to the external source/controller via a wire 618 arranged within the elongate body 602. In certain instances and as noted above, the electric field may be generated by applying direct current to the electrode 612. The use of direct current may cause apoptotic cell death to the tissue receiving the ablation energy. The direct current may form pores in the cells of the tissue region such that are irreversible (e.g., the pores do not close). The balloon structure 604 being in contact with the tissue may provide controlled and direct ablation of a target area while mitigating against down-stream proliferation of the ablation energy. In addition, the apparatus 600 may include a contrast port 628 arranged with the tip electrode 616. The contrast port 628 may be configured to eject contrast therethrough to assist in visualization of the apparatus 600 prior to and during ablation. The contrast port 628 may be off-set from a central axis of the elongate body 602. In certain instances, the tip electrode 616 may include multiple off-set contrast ports 628 to facilitate guidance into multiple side branch areas.

The electric energy can be transmitted to the tissue region (e.g., the vessel wall) via the liquid that permeates through the first portion 606 of the balloon structure 604. The electric field may modulate the activity along neural fibers within the wall of the tissue by at least partially causing apoptotic cell death to the tissue receiving the ablation energy. In certain instances while the electric field for ablation is being applied, transmission of the liquid from the first portion 606 of the balloon structure 604 to the tissue can be continued. The ablation process applied via the electrode 612 may be performed simultaneously and concurrently with the delivery of an antimitotic pharmacological agent as the liquid (or a saline and antimitotic pharmacological agent combination) to the tissue receiving the ablation energy or the ablation process can be performed sequentially with the delivery of the liquid.

The apparatus 600 may include pacing electrodes 620, 622 arranged within the balloon structure 604. The pacing electrodes 620, 622 may be electrically coupled to a mapping signal processor such that electrical events in myocardial tissue can be sensed for the generation of electrograms, monophasic action potentials (MAPs), isochronal electrical activity maps, and the like. The pacing electrodes 620, 622 may allow the physician to measure the electrical activity of the tissue region (e.g., the lack of electrical activity indicates ablated tissue, whereas the presence of electrical activity indicates live tissue) and determine a target location for the ablation therapy.

In certain instances, the apparatus 600 may include a steering mechanism 630. The steering mechanism 630 may be configured to direct the balloon structure 604, the elongate body 602, or both the balloon structure 604, and the elongate body 602. As shown in FIG. 6, the steering mechanism 630 is arranged centrally within the elongate body 602. The steering mechanism 630 may direct the balloon structure 604 and/or the elongate body 602 in multiple directions based on a force applied thereto. The steering mechanism 630 may be a wire that is coupled to a catheter handle (e.g., as shown in FIG. 1).

FIG. 7 shows a partial cross-sectional illustration of another exemplary apparatus 700 for applying ablation therapy to a tissue region in accordance with embodiments of the disclosure. The apparatus 700 includes a catheter having an elongate body 702 and a balloon structure 704 attached to the elongate body 702. The balloon structure 704 may be configured to inflate in response to a liquid or inflation medium. In addition, the balloon structure 704 may include a first portion 706 and a second portion 708. In certain instances, the first portion 706 of the balloon structure 704 may be configured to permeate a liquid therethrough (in response to inflation of the balloon structure 704) and the second portion 708 of the balloon structure 704 may be to anchor the elongate body 702 at the tissue region.

The balloon structure 704 may be positioned at or within the tissue region for ablation. In certain instances, the tissue region may be a vessel such as a pulmonary vein or a renal vein. The first portion 706 may permeate the liquid to the tissue region (e.g., the vessel wall). The liquid may include an anti-stenotic agent that mitigates against stenosis within the vessel. In addition, the second portion 708 may anchor the elongate body 702 within the vessel.

Electric energy can be transmitted to the tissue region (e.g., the vessel wall) via the liquid that permeates through the first portion 706 of the balloon structure 704. The electric field may modulate the activity along neural fibers within the wall of the tissue by at least partially causing apoptotic cell death to the tissue receiving the ablation energy. In certain instances while the electric field for ablation is being applied, transmission of the liquid the first portion 706 of the balloon structure 704 to the tissue can be continued. The ablation process applied via an electrode 712 may be performed simultaneously and concurrently with the delivery of an antimitotic pharmacological agent as the liquid (or a saline and antimitotic pharmacological agent combination) to the tissue receiving the ablation energy or the ablation process can be performed sequentially with the delivery of the liquid. The electrode 712, arranged with the elongate body 702 within the first portion 704, is configured to deliver energy to a tissue region. The ablation energy from the electrode 712 may be applied through an external surface of the first portion 706 of the balloon structure 704 by an electric field generated by an external source/controller and transferred through a wire 714 within the elongate body 702. In certain instances and as noted above, the electric field may be generated by applying direct current to the electrode 712. The use of direct current may cause apoptotic cell death to the tissue receiving the ablation energy. The direct current may form pores in the cells of the tissue region such that are irreversible (e.g., the pores do not close). The balloon structure 704 being in contact with the tissue may provide controlled and direct ablation of a target area while mitigating against down-stream proliferation of the ablation energy.

A tip electrode 716 may also be used to form a ground or a closed-loop with the electrode 712. The tip electrode 716 may also be coupled to the external source/controller. In addition, the apparatus 700 may include a contrast port 710 arranged with the tip electrode 716. The contrast port 710 may be configured to eject contrast therethrough to assist in visualization of the apparatus 700 prior to and during ablation. The contrast port 710 may be arranged at a distal end of the tip electrode 716.

Pacing electrodes 720, 722 arranged within the balloon structure 704 may be configured to determine electrical activity of the tissue region. The pacing electrodes 720, 722 may be used prior to ablation to estimate an extent tissue damage. In addition, the pacing electrodes 720, 722 may be used after the ablation to determine the extent of the ablation. The pacing electrodes 720, 722 may be electrically coupled to a mapping signal processor such that electrical events in myocardial tissue can be sensed for the generation of electrograms, monophasic action potentials (MAPs), isochronal electrical activity maps, and the like. The pacing electrodes 720, 722 may allow the physician to measure the electrical activity of the tissue region (e.g., the lack of electrical activity indicates ablated tissue, whereas the presence of electrical activity indicates live tissue) and determine a target location for the ablation therapy.

In certain instances, the apparatus 700 may be steerable and include a first steering wire 724 and a second steering wire 726. The first steering wire 724 and the second steering wire 726 may be configured to direct the balloon structure 704, the elongate body 702, or both the balloon structure 704 and the elongate body 702. The first steering wire 724 and the second steering wire 726 are arranged within the elongate body 702 on either side of a central lumen 728. As described in detail above, the central lumen 728 may include portions that carry liquid to each of the first portion 706 and the second portion 708. The first steering wire 724 and the second steering wire 726 may direct the balloon structure 704 and/or the elongate body 702 in multiple directions based on a force applied thereto. The first steering wire 724 and the second steering wire 726 may be coupled to a catheter handle (e.g., as shown in FIG. 1).

In certain instances, one or both of the first portion 706 and the second portion 708 may include a stent support structure 730. The stent support structure 730 may enhance the structural stability of one or both of the first portion 706 and the second portion 708.

FIG. 8 shows a partial cross-sectional illustration of another exemplary apparatus for applying ablation therapy to a tissue region accordance with embodiments of the disclosure. The apparatus 800 includes a catheter having an elongate body 802 and a balloon structure 804 attached to the elongate body 802. The balloon structure 804 may include a first portion 806 and a second portion 808. In certain instances, the first portion 806 of the balloon structure 804 may be configured to permeate a liquid therethrough and the second portion 808 of the balloon structure 804 may be to anchor the elongate body 802 at the tissue region in response to inflation of the balloon structure 804). The balloon structure 804 may be positioned at or within the tissue region for ablation. In certain instances, the tissue region may be a vessel such as a pulmonary vein or a renal vein. The first portion 806 may permeate the liquid to the tissue region (e.g., the vessel wall). The liquid may include an anti-stenotic agent that mitigates against stenosis within the vessel. In addition, the second portion 808 may anchor the elongate body 802 within the vessel.

Electric energy can be transmitted to the tissue region (e.g., the vessel wall) via the liquid that permeates through the first portion 806 of the balloon structure 804. The electric field may modulate the activity along neural fibers within the wall of the tissue by at least partially causing apoptotic cell death to the tissue receiving the ablation energy. In certain instances while the electric field for ablation is being applied, transmission of the liquid the first portion 806 of the balloon structure 804 to the tissue can be continued. The ablation process applied via an electrode 812 may be performed simultaneously and concurrently with the delivery of an antimitotic pharmacological agent as the liquid (or a saline and antimitotic pharmacological agent combination) to the tissue receiving the ablation energy or the ablation process can be performed sequentially with the delivery of the liquid. The ablation energy from the electrode 812 may be applied through an external surface of the first portion 806 of the balloon structure 804 by an electric field generated by an external source/controller and transferred through a wire 814 within the elongate body 802.

A tip portion 810 of the apparatus 800 may be configured to facilitate position of the balloon structure 804 at the tissue region. The tip portion 810 may include a central aperture 816 that may assist in passing the elongate body 802 and the balloon structure 804 through a puncture in an atrial septum to access the left atrium of a patient's heart. The central aperture 816 may pass a guidewire therethrough to assist in positioning of the tip portion 810 at the septum. Subsequently, a puncture tool may be arranged through the elongate body 802 and through the central aperture 816 to puncture the septum. The central aperture 816 may also be configured to eject contrast therethrough to assist in visualization of the apparatus 800 prior to and during ablation.

A visualization element 824 may also be used to assist in visualization. The visualization element 824 may include a camera and a light source (e.g., a light emitting diode (LED)). The visualization element 824 may be arranged with the elongate body 802 and configured to view and provide an image of video to a physician operating the apparatus 800. After positioning of the balloon structure 804 at the tissue region such as within the pulmonary vein (as shown in FIG. 2), the balloon structure 804 may be expanded. The inflation of the balloon structure 804 may cause the outer surface of the balloon structure 804 to contact an inner wall of the vessel. More specifically, the second portion 808 of the balloon structure 804 may anchor the elongate body 802 within the vessel. The visualization element 824 may be used to observe blood flow through the tissue area. In certain instances, the second portion 808 may block blood from through the tissue area such that the liquid eluted from the first portion 806 is directly applied to the tissue area. Blocking blood flow may mitigate against the liquid (e.g., anti-stenotic pharmaceutical agent) being carried from the tissue region. The anti-stenotic pharmaceutical liquid that may contact the tissue region (the inner wall of the vessel) and mitigate against stenosis formation that may result from the application of ablation energy applied via the electrode 812.

Pacing electrodes 820, 822 arranged within the balloon structure 804 may be configured to determine electrical activity of the tissue region. The pacing electrodes 820, 822 may be used prior to ablation to estimate an extent tissue damage. In addition, the pacing electrodes 820, 822 may be used after the ablation to determine the extent of the ablation. The pacing electrodes 820, 822 may be electrically coupled to a mapping signal processor such that electrical events in myocardial tissue can be sensed for the generation of electrograms, monophasic action potentials (MAPs), isochronal electrical activity maps, and the like. The pacing electrodes 820, 822 may allow the physician to measure the electrical activity of the tissue region (e.g., the lack of electrical activity indicates ablated tissue, whereas the presence of electrical activity indicates live tissue) and determine a target location for the ablation therapy.

The illustrative components shown in FIGS. 6-8 are not intended to suggest any limitation as to the scope of use or functionality of embodiments of the disclosed subject matter. Neither should the illustrative components be interpreted as having any dependency or requirement related to any single component or combination of components illustrated therein. Additionally, any one or more of the components depicted in any of the FIGS. 6-8 may be, in embodiments, integrated with various other components depicted therein (and/or components not illustrated), all of which are considered to be within the ambit of the disclosed subject matter. For example, the pacing electrodes 520, 522 may be used in connection with apparatus 300 and apparatus 400. In addition, apparatus 300 and apparatus 400 may include steering mechanisms and/or visualization elements as described with reference to FIGS. 6-8. Further, the tip sections of the apparatuses 600-800 may be collapsible as described above with reference to FIG. 5.

FIG. 9A shows a partial cross-sectional illustration of another exemplary apparatus 900 for applying stenosis prevention to a tissue region having a first multiple chamber configuration in accordance with embodiments of the disclosure. The apparatus 900 may include an elongate body 902 and a balloon structure 904. In the first multiple chamber configuration shown in FIG. 9A, the balloon structure 904 may include two chambers 906, 908 that are configured to anchor the elongate body 902 at the tissue region. The chambers 906, 908 may be impermeable to liquid applied to inflate the balloon structure 904. The balloon structure 904 may also include a third chamber 910 that is configured to permeate a liquid therethrough. The liquid may be an anti-stenotic agent and may prevent stenosis formation at the tissue region.

FIG. 9B shows the apparatus 900 for applying stenosis prevention, as shown in FIG. 9A, having a second multiple chamber configuration in accordance with embodiments of the disclosure. In the second multiple chamber configuration shown in FIG. 9B, the balloon structure 904 may include two chambers 906, 908 that are configured to anchor the elongate body 902 at the tissue region. The chambers 906, 908 may be impermeable to liquid applied to inflate the balloon structure 904. The third chamber 910 that is configured to permeate a liquid therethrough. The liquid may be an anti-stenotic agent and may prevent stenosis formation at the tissue region. The chambers 906, 908 are smaller than the first configuration chambers 906, 908 to allow for a larger third chamber 910.

FIG. 9C shows the apparatus 900 for applying stenosis prevention, as shown in FIGS. 9A-B, having a third multiple chamber configuration in accordance with embodiments of the disclosure. In the third multiple chamber configuration shown in FIG. 9B, the balloon structure 904 may include three chambers 906, 908, 912 that are configured to anchor the elongate body 902 at the tissue region. The chambers 906, 908, 912 may be impermeable to liquid applied to inflate the balloon structure 904. The apparatus includes the third chamber 910 configured to permeate a liquid therethrough and a fourth chamber 914 that is also configured to permeate a liquid therethrough. The liquid may be an anti-stenotic agent and may prevent stenosis formation at the tissue region. In the third configuration, the apparatus 900 includes two regions of permeability 916, 918 through which the liquid (e.g., the anti-stenotic agent) may permeate. Any of the first, second, and third configurations of the apparatus 900 may also include electrodes that are configured to apply ablation energy, as described in detail above. The electrodes may be arranged within the chambers that permeate the liquid.

Figure 10:
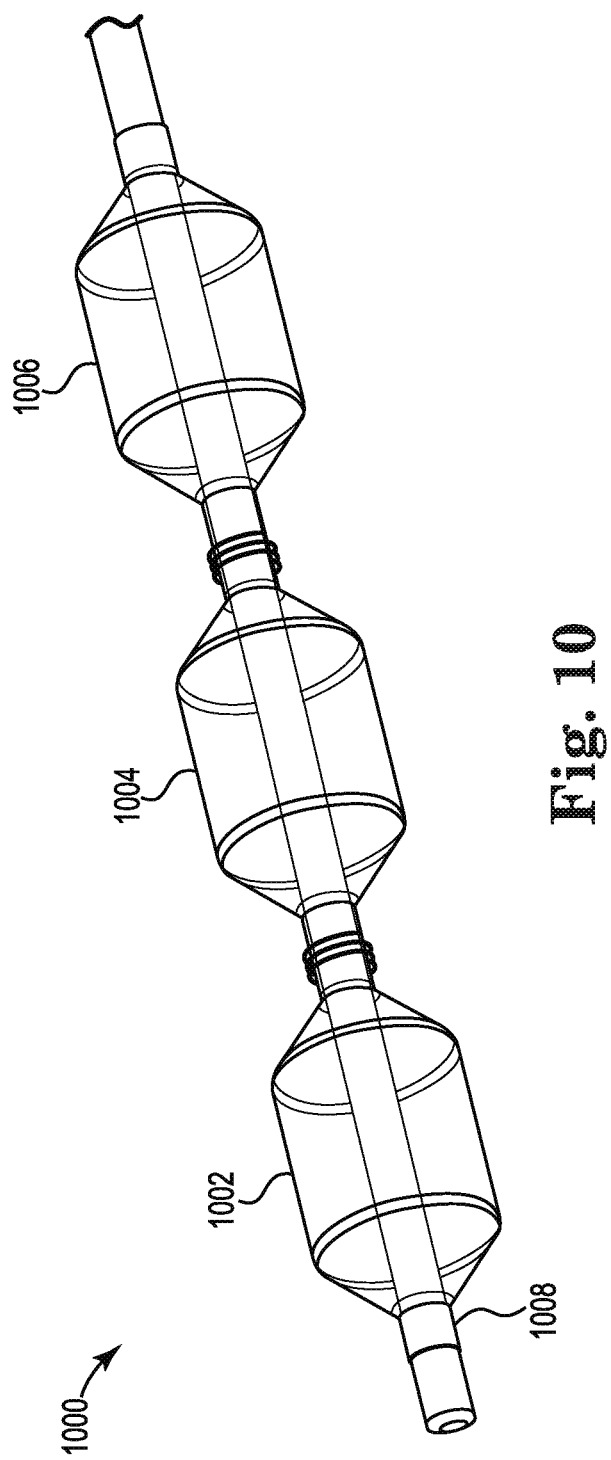
FIG. 10 shows another exemplary apparatus for applying stenosis prevention to a tissue region having a multiple chamber configuration in accordance with embodiments of the disclosure.

FIG. 10 shows another exemplary apparatus 1000 for applying stenosis prevention to a tissue region having a multiple chamber configuration in accordance with embodiments of the disclosure. The apparatus 1000 includes three chambers 1002, 1004, 1006 along an elongate body 1008 of a catheter. Each of the three chambers 1002, 1004, 1006 may be configured to permeate an anti-stenotic liquid therethrough. In certain instances, the entirety of the three chambers 1002, 1004, 1006 may be permeable to the liquid, and in other instances, only a portion of the three chambers 1002, 1004, 1006 may be permeable to the liquid. The permeability (or lack thereof) may differ between the three chambers 1002, 1004, 1006. Any of the three chambers 1002, 1004, 1006. may also include electrodes that are configured to apply ablation energy, as described in detail above.

Figure 11A:
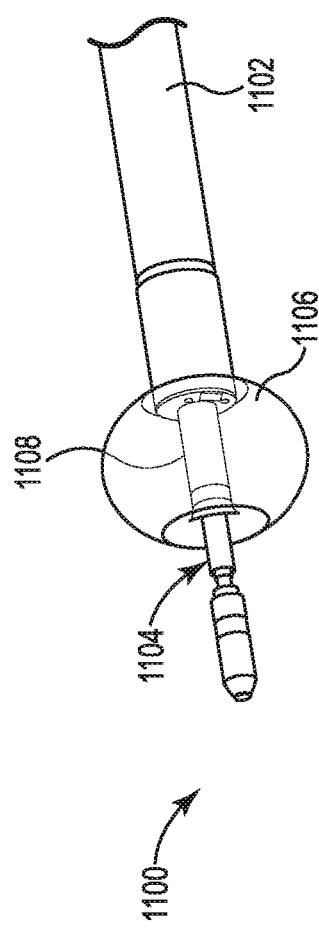
FIG. 11A shows another exemplary apparatus for applying ablation therapy to a tissue region having a telescoping balloon in a first configuration in accordance with embodiments of the disclosure.

FIG. 11A shows another exemplary apparatus 1100 for applying ablation therapy to a tissue region accordance with embodiments of the disclosure. The apparatus 1100 may include a catheter having an elongate body 1102 and a balloon structure 1104 attached to the elongate body 1102. The balloon structure 1104 may be configured to telescope from the elongate body 1102 prior to inflation thereof. As shown in FIG. 11A, the balloon structure 1104 is arranged in a first configuration prior to telescoping from the elongate body 1102.

A second balloon structure 1106 may be arranged with the elongate body 1102. The second balloon structure 1106 may house a visualization element 1108. The visualization element 1108 may also be used to assist in visualization during the application of ablation therapy. The visualization element 1108 may include a camera and a light source (e.g., a light emitting diode (LED)). The visualization element 1108 may be configured to view and provide an image of video to a physician operating the apparatus 1100.

In the first configuration, the elongate body 1102 and the catheter may be navigated to a tissue region. More specifically, the elongate body 1102 and the catheter may be navigated within the patient's heart. After navigating to the patient's heart (e.g. as described above with reference to FIG. 2), the balloon structure 1104 may be positioned at the tissue region. In certain instances, the tissue region may be a vessel such as a pulmonary vein. In these such instances, the balloon structure 1104 is arranged within the vessel.

Figure 11B:
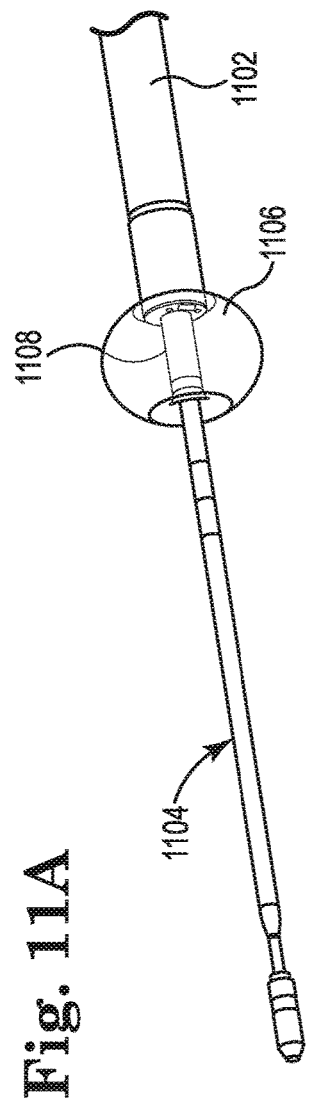
FIG. 11B shows the apparatus for applying ablation therapy, as shown in FIG. 11A, in a second configuration in accordance with embodiments of the disclosure.

FIG. 11B shows the apparatus 1100 for applying ablation therapy, as shown in FIG. 11A, in a second configuration in accordance with embodiments of the disclosure. In the second configuration, the balloon structure 1104 has been telescoped from the elongate body 1102 and has not yet been inflated. The positioning of the balloon structure 1104 at the tissue region (within the blood vessel) may occur during transition of the balloon structure 1104 between the first configuration and the second configuration, or after transition of the balloon structure 1104 to the second configuration. The balloon structure 1104 may include a section arranged within the elongate body 1102 that connects to a catheter handle. This section may be configured to slide within the elongate body 1102 to telescope the balloon structure 1104 therefrom.

Figure 11C:
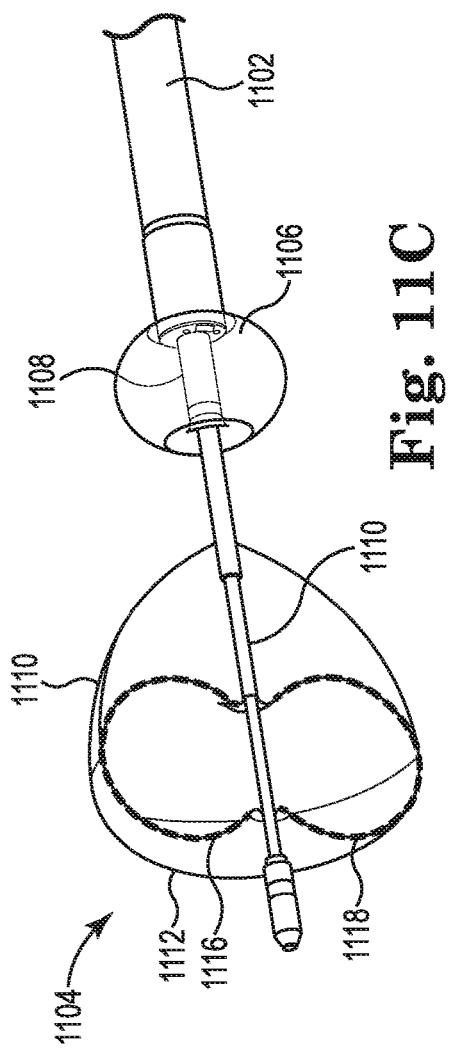
FIG. 11C shows the apparatus for applying ablation therapy, as shown in FIGS. 11A-B in a third configuration in accordance with embodiments of the disclosure.

FIG. 11C shows the apparatus 1100 for applying ablation therapy, as shown in FIGS. 11A-B in a third configuration in accordance with embodiments of the disclosure. In the third configuration, the balloon structure 1104 has been inflated. The balloon structure 1104 may include a first portion 1110 and a second portion 1112. In certain instances, the first portion 1110 of the balloon structure 1104 may be configured to permeate a liquid therethrough and the second portion 1112 of the balloon structure 1104 may be to anchor the elongate body 1102 at the tissue region in response to inflation of the balloon structure 1104). Thus, the first portion 1110 of the balloon structure 1104 may include a first permeability, and the second portion 1112 of the balloon structure 1104 may include a second permeability, with the first permeability being greater than the second permeability. The balloon structure 1104 may be positioned at or within the tissue region for ablation. In certain instances, the tissue region may be a vessel such as a pulmonary vein or a renal vein. The first portion 1110 may permeate the liquid to the tissue region (e.g., the vessel wall). The liquid may include an anti-stenotic agent that mitigates against stenosis within the vessel. In addition, the second portion 1112 may anchor the elongate body 1102 within the vessel.

An ablation process applied via an electrode 1114 may be performed simultaneously and concurrently with the delivery of an antimitotic pharmacological agent as the liquid (or a saline and antimitotic pharmacological agent combination) to the tissue receiving the ablation energy or the ablation process can be performed sequentially with the delivery of the liquid. Electric energy can be transmitted to the tissue region (e.g., the vessel wall) via the liquid that permeates through the first portion 1110 of the balloon structure 1104. The electric field may modulate the activity along neural fibers within the wall of the tissue by at least partially causing apoptotic cell death to the tissue receiving the ablation energy. In certain instances, while the electric field for ablation is being applied, transmission of the liquid the first portion 1110 of the balloon structure 1104 to the tissue can be continued. The ablation energy from the electrode 1114 may be applied through an external surface of the first portion 1110 of the balloon structure 1104 by an electric field generated by an external source/controller and transferred coupled to the electrode 1114.

After positioning of the balloon structure 1104 at the tissue region such as within the pulmonary vein (as shown in FIG. 2), the inflation of the balloon structure 1104 may cause the outer surface of the balloon structure 1104 to contact an inner wall of the vessel such. More specifically, the second portion 1112 of the balloon structure 1104 may anchor the elongate body 1102 within the vessel. The visualization element 1108 may be used to observe blood flow through the tissue area. In certain instances, the second portion 1112 may block blood from through the tissue area such that the liquid eluted from the first portion 1110 is directly applied to the tissue area. Blocking blood flow may mitigate against the liquid (e.g., anti-stenotic pharmaceutical agent) being carried from the tissue region. The anti-stenotic pharmaceutical liquid that may contact the tissue region (the inner wall of the vessel) and mitigate against stenosis formation that may result from the application of ablation energy applied via the electrode 1114.

In addition, the balloon structure 1104 may include pacing electrodes 1116, 1118 arranged therein. The pacing electrodes 1116, 1118 may be configured to determine electrical activity of the tissue region. The pacing electrodes 1116, 1118 may be used prior to ablation to estimate an extent tissue damage. In addition, the pacing electrodes 1116, 1118 may be used after the ablation to determine the extent of the ablation. The pacing electrodes 1116, 1118 may be electrically coupled to a mapping signal processor such that electrical events in myocardial tissue can be sensed for the generation of electrograms, monophasic action potentials (MAPs), isochronal electrical activity maps, and the like. The pacing electrodes 1116, 1118 may allow the physician to measure the electrical activity of the tissue region (e.g., the lack of electrical activity indicates ablated tissue, whereas the presence of electrical activity indicates live tissue).

In certain instances, when balloon structure 1104 is deployed (e.g., inside the pulmonary vein) the balloon structure 1104 may be positioned therein as distally as possible toward the bifurcation where the pulmonary vein splits. At this point, the second portion 1112 may be inflated first to anchor the elongate body 1102 therein. Inflation of the second portion 1112 may stop blood flow to the left atrium, which may be verified by the visualization element 1108. Subsequently, the pacing electrodes 1116, 1118 may measure the electrical activity of the pulmonary vein. The measurement by the pacing electrodes 1116, 1118 may provide a baseline for the ablation therapy. Ablation therapy may be applied via the electrode 1114, based on the measurement of the pacing electrodes 1116, 1118, along with release of an anti-stenotic via the liquid permeated through the first portion 1110. In certain instances, the liquid may be permeate through the first portion 1110 prior to the application of ablation therapy. The visualization element 1108 and/or an ultrasound may verify that the liquid (e.g., saline and the anti-stenotic) is flowing to the vessel wall prior to the application of ablation via the electrode 1114.

After ablation is applied, the pacing electrodes 1116, 1118 may be used again to measure the electrical activity. If the desired level of ablation has occurred based on the reading of the balloon structure 1104 may be deflated and removed from the pulmonary vein. In certain instances, the balloon structure 1104 may be moved along the pulmonary vein to a second ablation site. The second portion 1112 may remain inflated during repositioning of the balloon structure 1104. The electrical activity of the second ablation may be measured by the pacing electrodes 1116, 1118, and the liquid permeation and ablation may occur. This process may be repeated until the desired level of ablation is achieved. The movement to the second ablation site (e.g., 5 mm) may be determined based on a change in the electrical activity measured by the pacing electrodes 1116, 1118. In addition the electrode 1114 may apply electrical energy via direct current applied thereto at various pulse width patterns and amplitudes (e.g., 1-30 microsecond pulses at 1000-3000 volts). For further detail regarding the ablation procedure, including mapping use the pacing electrodes 1116, 1118, reference may be made to the FIG. 1 and the related discussion.

The illustrative components shown in FIGS. 11A-C are not intended to suggest any limitation as to the scope of use or functionality of embodiments of the disclosed subject matter. Neither should the illustrative components be interpreted as having any dependency or requirement related to any single component or combination of components illustrated therein. Additionally, any one or more of the components depicted in any of the FIGS. 11A-C may be, in embodiments, integrated with various other components depicted therein (and/or components not illustrated), all of which are considered to be within the ambit of the disclosed subject matter.

FIG. 12 shows an exemplary balloon structure 1200 for applying stenosis prevention to a tissue region in accordance with embodiments of the disclosure. The balloon structure 1200 may include a permeability portion 1202 and non-permeability portion 1204. The permeability portion 1202 may include a plurality of nanostructures 1206. In certain instances, the nanostructures 1206 may be hollow fibers that act as a core material to contain a liquid, such as an anti-stenotic drug. In other instances, the plurality of nanostructures 1206 may contain a liquid, such as an anti-stenotic drug, in gaps between the plurality of nanostructures 1206. The plurality of nanostructures 1206 in either instance may form a cross-hatched network within the permeability portion 1202.

The plurality of nanostructures 1206 may be arranged on the balloon structure 1200 by fiber deposition, fiber sintering (thermal or chemical), hydrophilic or hydrophobic coating, or other similar processes. In addition, the permeability portion 1202 may include multiple layers such that one layer may include the plurality of nanostructures 1206, and another layer is arranged thereon to mitigate against release of the liquid from the plurality of nanostructures 1206. The liquid may release from the plurality of nanostructures 1206, with or within the layer arranged thereon, in response to inflation of the balloon structure 1200. The liquid, such as the anti-stenotic drug, may be delivered to a tissue region by diffusion into the tissue, or may be driven by ionophoresis by an electrical force originating from an electrode (not shown) arranged within the balloon structure 1200. In other instances, the plurality of nanostructures 1206 may be replaced with a coating on the balloon structure 1200 of the anti-stenotic drug. This may include combing the anti-stenotic drug with water or saline (e.g., 4.86% 80/20 ptx/ATBC in 40/40/20 EtOH/Acetone/water). In certain instances, the balloon structure 1200 may have multiple layers. One or more anti-stenotic drugs, saline or other pharmacological agents may be impregnated within the different layers of the balloon structure 1200. Sequential delivery of the anti-stenotic drugs, saline or other pharmacological agents may be delivered via the different layers of the balloon structure 1200. In addition, the balloon structure 1200 may have different layers in different portions thereof for sequential delivery of the anti-stenotic drugs, saline or other pharmacological agents.

The illustrative components shown in FIG. 12 are not intended to suggest any limitation as to the scope of use or functionality of embodiments of the disclosed subject matter. Neither should the illustrative components be interpreted as having any dependency or requirement related to any single component or combination of components illustrated therein. Additionally, any one or more of the components depicted in any of the FIG. 12 may be, in embodiments, integrated with various other components depicted therein (and/or components not illustrated), all of which are considered to be within the ambit of the disclosed subject matter. For example, the nanostructures 1206 may be used in connection with any of the balloon structures discussed herein.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. An apparatus for applying ablation therapy to a tissue region, the apparatus comprising:
   a catheter sized and shaped for vascular access and including an elongate body extending between a proximal end and a distal end;
   a balloon structure arranged near the distal end of the elongate body and having a first portion and a second portion, the first portion of the balloon structure being configured to permeate a liquid therethrough and the second portion of the balloon structure being configured to anchor the elongate body at the tissue region;
   one or more mapping electrodes arranged on or within the balloon structure and configured to determine a target location for the ablation therapy;
   one or more electrodes arranged on or within the balloon structure and configured to deliver energy to the tissue region; and
   a tip electrode arranged at the distal end of the catheter and configured to form a ground or a closed-loop with the one or more electrodes.

2. The apparatus of claim 1, wherein an external surface of the first portion of the balloon structure is configured to transfer the energy from the one or more electrodes to the tissue region.

3. The apparatus of claim 2, wherein the one or more electrodes comprises an electrode arranged within the first portion of the balloon structure.

4. The apparatus of claim 3, wherein the electrode is configured to deliver the energy via the first portion of the balloon structure in response to a direct current applied thereto.

5. The apparatus of claim 4, wherein the liquid comprises at least one of saline, a pharmacological agent, and an anti-stenotic agent, and the liquid is configured to mitigate against stenosis at the tissue region.

6. The apparatus of claim 1, wherein the second portion of the balloon structure is arranged within the first portion of the balloon structure.

7. The apparatus of claim 6, wherein the first portion forms a first chamber of the balloon structure, and the second portion forms a second chamber of the balloon structure.

8. The apparatus of claim 7, wherein the elongate body includes a first opening arranged within the first chamber and the elongate body includes a second opening arranged within the second chamber, the first portion is configured to elute a liquid therethrough in response to influx of the liquid into the first chamber through the first opening, and the second portion is configured to expand and anchor the elongate body at the tissue region in response to influx of a second liquid into the second chamber through the second opening.

9. The apparatus of claim 1, wherein the balloon structure is configured to telescope from the elongate body prior to inflation thereof.

10. The apparatus of claim 1, further comprising a steering mechanism configured to direct at least one of the balloon structure and the elongate body.

11. The apparatus of claim 10, wherein the steering mechanism comprises at least one wire coupled to a catheter handle.

12. An apparatus for applying ablation therapy to a tissue region, the apparatus comprising:
    a catheter sized and shaped for vascular access and including an elongate body extending between a proximal end and a distal end;
    a balloon structure arranged near the distal end of the elongate body and having a first portion with a first permeability and a second portion with a second permeability, the first permeability differing from the second permeability;
    one or more electrodes arranged on or within the balloon structure configured to determine a target location for the ablation therapy and to deliver energy to the tissue region based on the determined location; and
    a tip electrode arranged at the distal end of the catheter and configured to form a ground or a closed-loop with the one or more electrodes.

13. The apparatus of claim 12, wherein the first portion of the balloon structure is configured to elute a first liquid therethrough, and the first liquid is configured to mitigate against stenosis at the tissue region.

14. The apparatus of claim 13, wherein the second portion of the balloon structure is configured to anchor the elongate body at the tissue region in response to a second liquid expanding the second portion.

15. The apparatus of claim 14, further comprising a visualization element arranged with the elongate body, and the visualization element is configured to observe blood flow through the tissue area.

16. The apparatus of claim 15, wherein the tissue region is at least one of a pulmonary vein and a renal vein, and the first portion of the balloon structure and the one or more electrodes are configured to elute the first liquid and deliver the energy simultaneously.

17. A method for applying ablation therapy to a tissue region within a patient's heart, the method comprising:
    navigating a catheter within the patient's heart, the catheter including an elongate body extending between a proximal end and a distal end;
    positioning a balloon structure at the tissue region, the balloon structure being arranged near the distal end of the elongate body and having a first portion with a first permeability and a second portion with a second permeability, the first permeability differing from the second permeability;
    determining a pacing of the tissue region via one or more mapping electrodes arranged on or within the balloon structure to determine a target location for the ablation therapy;
    delivering energy to the tissue region based on the determined location via one or more electrodes arranged on or within the balloon structure and a tip electrode arranged at the distal end of the catheter and configured to form a ground or a closed-loop with the one or more electrodes; and eluting a liquid through the first portion of balloon structure during delivery of the energy to the tissue region.

18. The method of claim 17, further comprising anchoring the elongate body within the tissue region by inflating the second portion of the balloon structure.

19. The method of claim 18, further comprising visualizing flow within the tissue region subsequent to anchoring the elongate body within the tissue region.

20. The method of claim 19, wherein the liquid comprises at least one of saline, a pharmacological agent, and an anti-stenotic agent, and the liquid is configured to mitigate against stenosis at the tissue region.

* * * * *